US00PP23674P2

(12) United States Plant Patent
Jeske et al.

(10) Patent No.: US PP23,674 P2
(45) Date of Patent: Jun. 18, 2013

(54) HOP PLANT NAMED 'DELTA'

(50) Latin Name: *Humulus lupulus* L
Varietal Denomination: Delta

(75) Inventors: Roger D. Jeske, Yakima, WA (US); Paul D. Matthews, Yakima, WA (US)

(73) Assignee: S.S. Steiner, Inc., New York, NY (US)

( * ) Notice: Subject to any disclaimer, the term of this patent is extended or adjusted under 35 U.S.C. 154(b) by 13 days.

(21) Appl. No.: 12/932,034

(22) Filed: Feb. 16, 2011

(51) Int. Cl.
*A01H 5/00* (2006.01)

(52) U.S. Cl.
USPC ..... Plt./236

(58) Field of Classification Search
USPC ..... Plt./236
See application file for complete search history.

(56) References Cited

U.S. PATENT DOCUMENTS

| | | | | |
|---|---|---|---|---|
| PP18,602 | P3 | 3/2008 | Jeske et al. | Plt./236 |
| PP20,200 | P3 | 8/2009 | Jeske et al. | Plt./236 |
| PP20,227 | P3 | 8/2009 | Jeske et al. | Plt./236 |

*Primary Examiner* — Kent L Bell
(74) *Attorney, Agent, or Firm* — Hayes Soloway P.C.

(57) ABSTRACT

A new and distinct aroma variety of hop plant, *Humulus lupulus* L., named 'Delta' is characterized by its good cone yield, nice aroma (characterized as mild citrus/spice), 1:1 ratio of alpha-acids to beta-acids, low CoH, high Linalool, good storage stability, and resistance to hop powdery mildew. The new variety resulted from cross-pollination performed in 2003 in a field in Prosser, Wash., United States and has been asexually reproduced in a nursery in Prosser, Wash., United States.

3 Drawing Sheets

BACKGROUND OF INVENTION

The flowers (cones) of the female hop plant, *Humulus lupulus* L, are used in the making of beverages, especially beer, as a flavoring and processing component. Hops contribute towards the bitterness and aroma in beer as well as foam quality and flavor and taste stability. Various hop varieties have various special uses in the beer brewing industry. Specialized "aroma" hops are used to impart flavors by virtue of the distinct profiles of their essential oils and terpene alcohols, among other compounds, as well as to supply bitter flavors based on specific contents of bitter acids, namely, terpenophenolics, mostly humulones. Examples of aroma hops are the cultivars known as variety 'Williamette' (non-patented), variety 'Fuggle' (non-patented) and variety 'Cascade' (non-patented). Many aroma varieties are susceptible to fungal pathogens and otherwise exhibit less than ideal agronomic traits. The present invention relates to a novel hop variety which retains the good "aroma" quality of the above mentioned varieties, yet has significant improvements in agronomic traits.

Hop plants, hops cones, male hop flowers, hop plant parts, hop tissue cultures and hop extracts also have bioactive properties; including anti-microbial, anti-cancer, anti-osteoporosis, anti-oxidative, anti-inflammatory, antibiotic, soporific, anti-androgenic, and pro-estrogenic activities, among others; which may be used in herbal remedies, in antimicrobial preparations for food, fodder, food fermentation, food process, animal husbandry; or in non-food uses, such as composting, bio-fuel processing, fermentation process, water treatment, animal bedding and phytoremediation; and uses in cosmetics, in nutraceutical and in pharmaceutical applications and in research thereof. Examples activities and non-beverage uses are included herein by references:

J Hazard Mater. Apr. 26;91(1-3):95-1 12; Mol Cancer Ther, Sep;1(11):959-69; Phytochemistry. May;65(10):1317-30; U.S. Pat. No. 6,423,317 (2002); U.S. Pat. No. 6,623,775 (2003).

Agricultural end-product users, growers, handlers and processors of hops, of hop plants, of hop tissues and of hop products use hops and are affected by the agronomic, developmental, morphological, chemical and physical properties that vary among unique and distinct asexually reproduced varieties. Users of hops are also interested in new combinations or mixtures of hop cultivars that improve the quality of beverage flavor and process and storage properties. This invention relates to a novel asexually produced hop variety, named 'Delta', invented in a planned and systematically executed breeding program.

SUMMARY OF INVENTION

This invention relates to a new genetically, chemically, and morphologically distinct variety of hop plant selected from among the multitude of hop plants resulting from a controlled cross-pollination during the summer of 2003. The cross-pollination was between a commercially available non-patented female hop plant referred to as 'Fuggle' (non-patented) with a proprietary non-patented male hop plant 'KA-0113m'. The parents of this male hop plant referred to as 'KA-0113m' are female hop plant 'Cascade' (non-patented) and a male hop plant 'USDA 19058m' (non-patented).

The cross-pollination resulting in 'Delta' was performed in 2003 by Roger Jeske, the named inventor, in a field in Prosser, Wash. During 2004 seeds collected from the cross-pollination were germinated and screened for powdery mildew resistance in a greenhouse in Prosser, Wash. These seedlings were planted in a field nursery and further screened for gender, vigor, cone type, and disease resistance with the best genotypes being advanced to a single hill hop nursery during the spring of 2005. Mr. Jeske discovered the 'Delta' variety during the summer of 2005 among the numerous hop genotypes growing in a single hill hop nursery in Prosser, Wash. These hop genotypes growing in the single hill hop nursery were grown in a 3.5 foot by 14 foot spacing on twine attached to an 18 foot trellis system. Chemical analysis and field observations in 2005 and 2006 demonstrated a lack of powdery mildew in the leaves and cones, an exceptional cone set, a pleasant, slightly citrus/spice aroma in the mature cones, and a 1:1 ratio of alpha-acids to beta-acids. Cones were numerous and easy to pick with no shatter. Vigor was excellent and yield potential appeared to be exceptional for an aroma variety. Although yield data was not taken from the single hill plot in 2005, the 2006 single hill yield calculated to approximately 2,000-2,100 pounds per acre.

In March and April, 2006, 'Delta' was asexually propagated in greenhouses at Prosser, Wash. Rhizomes from the original single hill plant of 'Delta' were dug, and planted into four greenhouse grown containers. Softwood cuttings were used from these four original containers until approximately 48 softwood-cutting plants were made. These softwood cutting plants constituted the first asexual reproduction of the 'Delta' variety and are the second generation. They were grown at two distinct geographical locations with no powdery mildew observed during 2006 or any subsequent years. These two small scale trials consisted of a multi-hill planting (14 plants) located in a field in Prosser, Wash. and a multi-hill planting (16 plants) in a field located in Sunnyside, Wash. These trials were subjected to standard agronomic, cultural and management practices for the purposes of determining yield, disease tolerance, chemical characteristics, and adaptability of 'Delta' to various soils, geographical locations, and cultural practices.

During 2006, 2007, 2008, 2009, and 2010 second-generation plants in the two small-scale trials were observed for disease, sampled for chemical analysis, and harvested for yield evaluations. Results from the test plots provided additional information supporting the disease resistance, yield potential, alpha-acids, beta-acids, and aroma projections made from the original 'Delta' plant (first generation) selected in 2005. This confirmed the disease resistance, good yield, pleasant citrus/spice aroma, and a 1:1 ratio of alpha-acids to beta-acids. The 2007-2010 harvest of second generation plants of 'Delta' grown in multi-hill plantings, yielded 1,800-2,200 pounds per acre.

In 2007, the second asexual reproduction of the 'Delta' variety took place. Rhizomes from the second-generation rootstock from the multi-hill plants were dug, divided and planted into greenhouse grown containers. Softwood cuttings were taken from these containers until approximately 2,000 softwood-cutting plants were made. These third generation plants were planted into a one acre plot in a field near Prosser, Wash. in a 3.5 foot by 14 foot configuration (889 hills per acre), with two softwood cuttings planted per hill. This one acre trial was subjected to standard agronomic, cultural and management practices for the purposes of determining commercial harvest ability, yield, chemical characteristics, and process ability. Third generation plants were sampled for chemical analysis and harvested for yield evaluations. Results from this third generation large-scale test plot provided additional information supporting the powdery mildew resistance and aroma characteristics of 'Delta'. The 2007 yield from these baby plants was 1,200 pounds per acre, which is very good as compared to the baby yield of other commercially grown aroma varieties. The 2008 commercially harvested one-acre test plot of mature 'Delta' plants produced an average of 1,660 lbs/acre. Bale samples showed an alpha-acid of 6.5% and beta-acid of 7.0% (American Society of Brewing Chemists spectrophotometric method).

In 2008, the multi-hill plots of 'Delta' that were being grown in the fields at Prosser and Sunnyside, Wash., were expanded to two other distinct geographical locations in Idaho's Treasure Valley and Oregon's Willamette Valley. These two small scale trials consisted of a multi-hill planting (14 plants) located in a field in Wilder, Id. and a multi-hill planting (20 plants) located in a field in Silverton, Oreg. These trials were subjected to standard agronomic, cultural and management practices for the purposes of determining yield, disease tolerance, chemical characteristics, and adaptability of 'Delta' to various soils, geographical locations, day lengths, and cultural practices in other hop growing states. During 2009 and 2010, second-generation plants in the two small-scale trials in Idaho and Oregon were observed for disease, sampled for chemical analysis, and harvested for yield evaluations. Results from the Idaho and Oregon test plots provided additional information supporting and confirming the powdery mildew disease resistance, good yield, mild and pleasant citrus/spice aroma, and 1:1 ratio of alpha-acids to beta-acids. The harvest of third generation plants of 'Delta' grown in multi-hill plantings in Idaho and Oregon yielded 2,000-2,200 pounds per acre in both 2009 and 2010.

Based on agronomic and chemical evaluations over a number of growing seasons and geographic locations, both secondary and tertiary plants (second and third generations) of 'Delta' exhibited genetic stability with respect to its novel characteristics of a mild-pleasant citrus/spice aroma, complete powdery mildew resistance, high yield for an aroma variety (averaging 2,000 pounds per acre), 6-7% alpha acids, 1:1 ratio of alpha-acids to beta-acids, and good storage stability. This is in contrast to the mother, 'Fuggle' (non-patented), which is slightly susceptible to powdery mildew, has a poor yield history, low alpha acid percentage and poor storage stability. 'Delta' has consistently yielded 50-60% higher with alpha acids levels 70-80% higher than its mother 'Fuggle' (non-patented). Also, storage stability of 'Delta' is 80% alpha retention versus 60% alpha retention for 'Fuggle' (non-patented) after 6 month storage @ 70° F.

All observations, evaluations and testing of the 'Delta' variety's agronomic, morphological, physical, and chemical properties were carried out by or directed by the inventor, Roger Jeske.

The variety 'Delta' is early maturing and is usually ready to pick by August 25-30th. The medium loose and ovoid shaped cones of this variety are medium to large sized and very plentiful resulting in fairly easy mechanical picking and cleaning. The cones detach easily from stems and the cones shatter very little during commercial harvesting and drying.

In order to demonstrate genetic and phenotypic distinctiveness to closely related varieties, 'Delta' is compared to its mother and other agronomically important varieties. 'Fuggle' (non-patented) is a parent of 'Delta' and therefore similarities would be expected. The primary differences between the new 'Delta' variety and 'Fuggle' (non-patented) is the complete resistance of 'Delta' to the powdery mildew strains found in Washington, Oregon and Idaho 'Delta' also has a higher yield, higher alpha percentage, and better storage stability of alpha acids as compared to 'Fuggle' (non-patented) and 'Williamette' (non-patented) 'Delta' mostly exhibits main bine leaves with 5 lobes as opposed to its parent 'Fuggle' (non-patented) with 3-5 lobes and 'Cascade' (non-patented) with 3 lobes. 'Delta' has a higher Linalool content (>1%), lower Farnesene content (<1%), and lower CoH (23%) when compared to 'Fuggle' (non-patented), 'Cascade' (non-patented), and 'Williamette' (non-patented). Similarities include early maturity and the good aroma characteristics found in 'Fuggle' (non-patented), 'Willamette' (non-patented), and 'Cascade' (non-patented). The ratio of humulene/caryophyllene is 2.7:3.0 and is very similar to 'Fuggle' (non-patented) and 'Williamette' (non-patented). 'DELTA' is comparable to its male parent in its vigorous growth habit and disease resistance. Both are resistant to hop powdery mildew strains found in Washington, Oregon and Idaho. Male hops are morphologically different than female hops, having no commercial value other than for passing on certain traits through cross breeding. Therefore, no other comparisons can be made between 'DELTA' and its male parent.

The detailed botanical description and drawings herein below allow distinction of the variety from related varieties.

BRIEF DESCRIPTION OF THE DRAWINGS

The accompanying photographs illustrate the cones, leaves and growth habit of the new 'Delta' variety.

GENERAL BOTANICAL DESCRIPTION OF THE VARIETY

Figure 1:
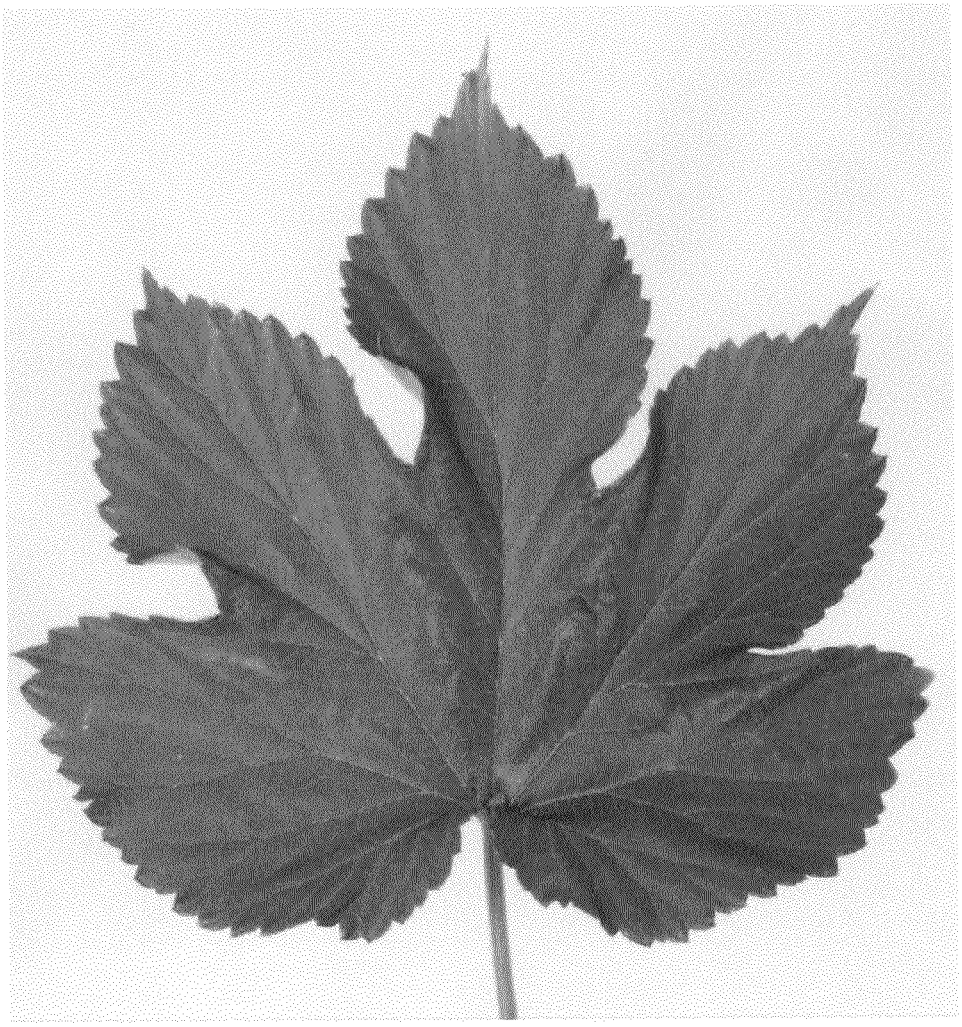
FIG. 1 depicts a close up of mature main vine leaf.
Figure 2:
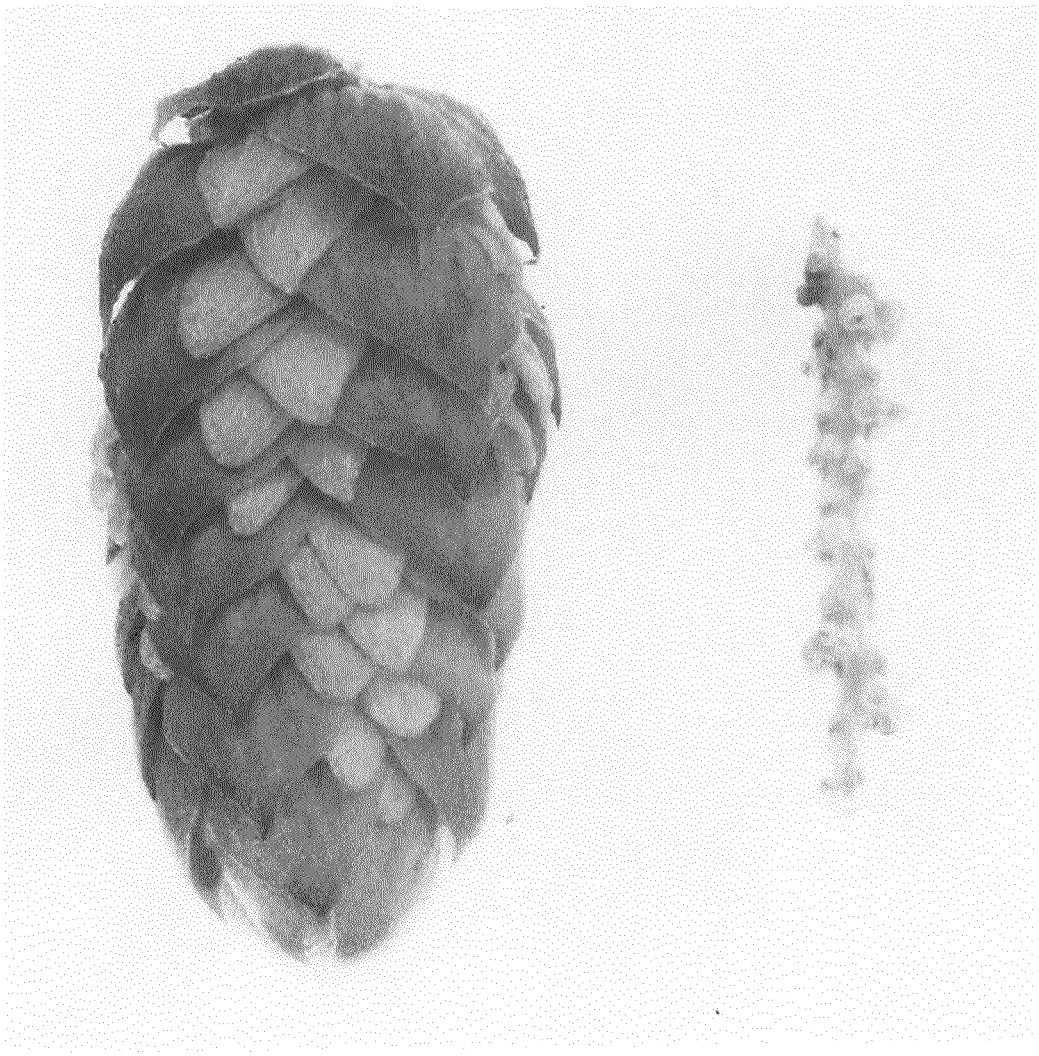
FIG. 2 depicts a close up of whole cone and strig.
Figure 3:
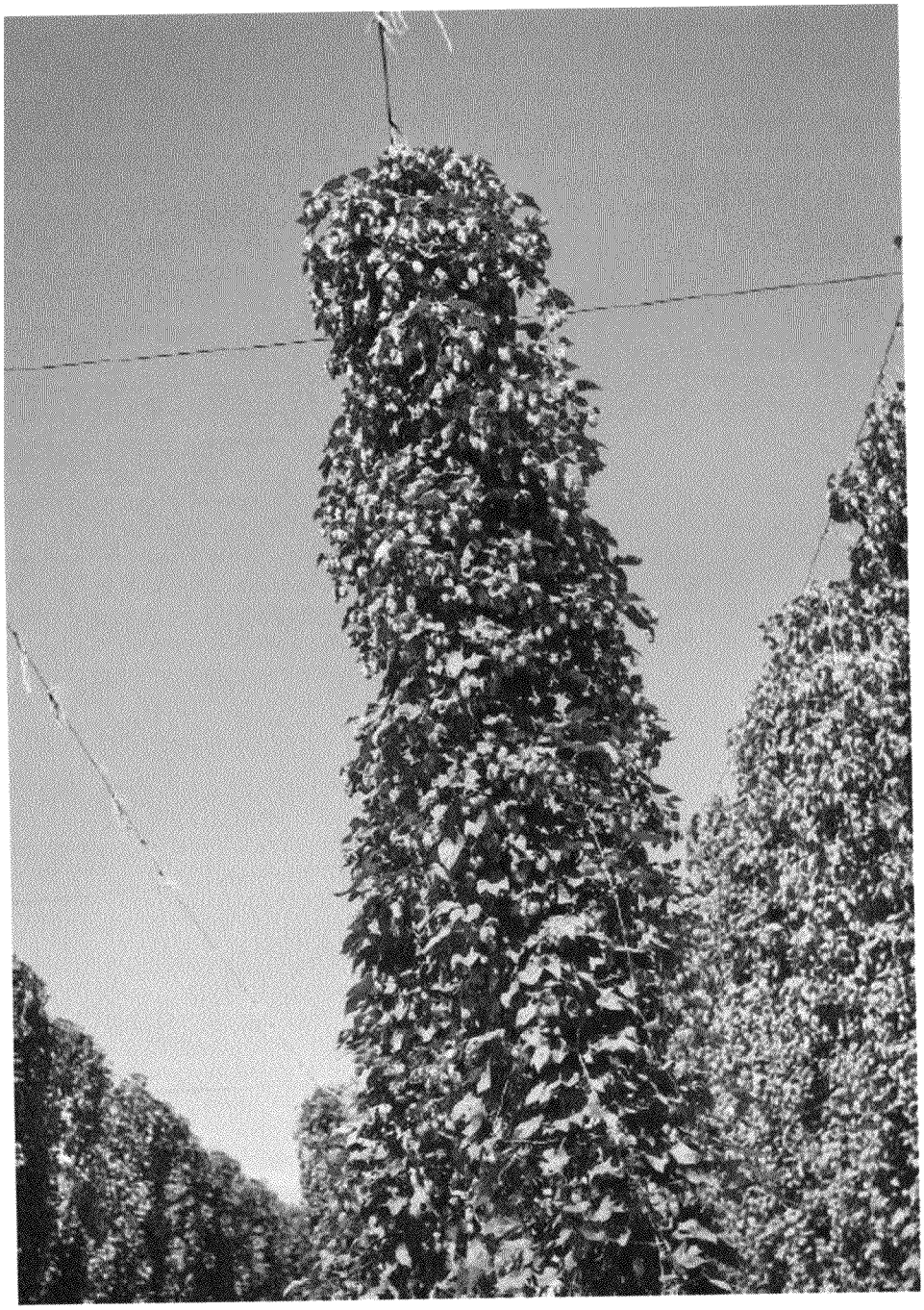
FIG. 3 depicts the appearance of the plants and cones as they are growing in the field on a high trellis (18 feet) approaching harvest time.

This description provides information on agronomic, morphological, chemical and processing characteristics of the new variety that are used in distinction and identification of a new hop variety and its parts and products by practitioners of the industries that use hops as described herein above.

General information on the botanical characteristics and cultural aspects of hop plants as they relate to agronomics, breeding and food use are particularly well discussed in the prior art, especially, U.S. Plant Pat. Nos. 10,956; 13,132; 18,039; 18,602; 20,200; and 20,227 and the literature; "Steiner's Guide to American Hops Book III", 1986; "Hops" Published by Chapman and Hall, 1991. Detailed botanical information below of the present variety is directly comparable to the prior art, as contained by reference herein.

DETAILED BOTANICAL DESCRIPTION OF THE VARIETY

Following is a detailed description of the botanical and analytical chemical characteristics of the new variety. The information for this botanical description was either collected or verified during the growing seasons of 2006 through 2010 in the growing areas north of Prosser, Wash.; south of Sunnyside, Wash.; north of Wilder, Id.; and northwest of Silverton, Oreg.

Botanical characteristics, and to a lesser degree the analytical characteristics, are somewhat dependent on cultural practices and climatic conditions and can vary with location or year:

1. Parentage: A hop plant originating from a controlled cross-pollination between a commercially available non-patented female hop plant referred to as 'Fuggle' (non-patented) with a proprietary non-patented male hop plant ('Cascade'×'USDA 1905m').
2. Locality where grown and observed: North of Prosser, Wash.; south of Sunnyside, Wash.; north of Wilder, Id.; and north west of Silverton, Oreg.
3. Agronomic factors: Dates of first and last harvest are approximately August 25$^{th}$ and September 5$^{th}$. Shoots of 'Delta' emerge from winter dormancy about one week prior to the commercial varieties 'Fuggle' and 'Willamette' (both non-patented). Emergence is typically by March 15$^{th}$ and the initial stem growth is fairly rapid like 'Zeus' or 'Nugget' (both non-patented). 'Delta' shows good vigor and a moderate growth rate. After spring pruning, growth continues to be above average when compared to other commercial varieties. The initial stem color and upper leaf surface during April are purple to violet (RHS N77B). This early season purple shading fades away and changes to a greenish hue as the hop vines grow longer. During the late summer, main vine stems are yellow-green (RHS 144B). 'Delta's' main vine stems are mostly round to slightly hexagonal in cross section shape with no pronounced stripes. Inflorescence of 'Delta' begins to appear in early to the middle of July and mature during the last week of August. Cone shape is fairly uniform in the 'Delta' variety. The hop cones of 'Delta' are well adapted to mechanical harvest because of their medium/large size, ovoid shape, and they roll nicely on dribble belts, making cleaning easy. The cones do not shatter during harvest unless they are seeded. In the following description color code designations are by reference to The R.H.S. Colour Chart, 4$^{th}$ Edition, provided by The Royal Horticultural Society of Great Britain.
4. Plant characteristics:
   - *Plant*.—Vigorous, climbing vine.
   - *Plant shape*.—Columnar.
   - *Bine color*.—Yellow-green (RHS 144B).
   - *Bine stripe*.—None.
   - *Bine inter-node length* (*at 6 feet high*).—21 cm.
   - *Bine diameter* (*at 6 feet high*).—1 cm.
   - *Bine length*.—19-20 feet.
   - *Petiole length*.—9 cm.
   - *Petiole diameter*.—0.2-0.3 cm.
   - *Petiole color*.—Yellow-green (RHS 145A).
   - *Petiole shape*.—Slightly channeled (flat upper surface).
   - *Leaf arrangement*.—Opposite.
   - *Mature leaf shape*.—Cordate.
   - *Mature leaf color*.—Upper surface dark green (RHS N137A).
   - *Mature leaf color*.—Lower surface green (RHS 137C).
   - *Mature leaf width*.—18-19 cm.
   - *Mature leaf length*.—14-15 cm.
   - *Number of main bine leaf lobes*.—Five (occasionally 3).
   - *Venation pattern*.—Netted (Palmately veined).
   - *Vein color*.—Green (RHS 145A).
   - *Leaf margin*.—Pronounced dentate which is fairly typical of most hop varieties.
   - *Leaf apex*.—Apical lobe or blade apex with marginal serrations.
   - *Lateral length* (*at 6 feet high*).—0.6-0.8 m.
   - *Lateral diameter* (*at 6 feet high*).—0.5-0.6 cm.
   - *Lateral color*.—Yellow-green (RHS 144B).
   - *Internode length of lateral* (*at 6 feet high*).—7-9 cm.
   - *Stipule position*.—Outward-up, forked.
   - *Stipule color*.—Yellow-green (RHS 146B).
5. Reproductive organs, cones, cone parts, seeds:
   - *Bract color* (*upper surface*).—Yellow-green (RHS 146B).

*Bract color* (*lower surface*).—Yellow-green (RHS 146A).

*Bract tips shape*.—Acute.

*Bract diameter*.—0.7-0.9 cm.

*Bract length*.—1.3-1.7 cm.

*Bract tip position*.—Mostly appressed like most hop varieties, as opposed to everted (turned out bracts) as seen in the variety of Galena.

*Bracteole diameter*.—0.7-0.9 cm.

*Bracteole length*.—1.4-1.8 cm.

*Bracteole shape*.—Lanceolate, similar to most hop varieties.

*Bracteole color* (*upper and lower surface*).—Yellow-green (RHS 145 B).

*Compactness*.—Semi-loose.

*Shape*.—Ovoid.

*Cone length*.—3-4 cm average for most hops, but range can be as much as 2-7 cm.

*Cone diameter*.—1.5-2.3 cm which can be quite variable between hop varieties.

*Cone tip shape*.—Bluntly pointed.

*Cone weight*.—200-240 mg, mid range for hop varieties that vary from 90-450 mg.

*Strig*.—small and semi-compact.

*Lupulin glands*.—The cone of the present variety contains a moderate amount of lupulin glands.

*Yield per acre*.—1600-2200 pounds on average. However, this yield is dependent upon temperature, soil conditions and cultural practices, and is therefore not distinctive of the present variety.

*Seeds*.—Highly variable in color and size depending on male parent.

*Date of maturity*.—Considered to be early (August 25$^{th}$ -September 5th) as compared to other common hop varieties grown in central Washington.

6. Analytical data of cones:

% *Alpha-acids* (*bale*).—5.5-7.0% (ASBC Spectrophotometric method).

% *Beta-acids* (*bale*).—5.5-7.0% (ASBC Spectrophotometric method).

*Alpha/beta ratio*.—1:1. Cohumulone "CoH" (% of alpha-acids): 22-24%.

*Storage characteristics*.—20% transformation of alpha acids after 6 months at 22 degrees C.

*Total oils* (*mls*/100 *g*).—0.6-1.1.

*Humulene* (% *of total oils*).—30-40%.

*Caryophyllene* (% *of total oils*).—9-15%.

*Humulene/caryophyllene ratio*.—0.9.

*Farnesene* (% *of total oils*).—<1.0%.

*Myrcene* (% *of total oils*).—25-40%.

7. Disease resistance: The variety 'Delta' is resistant to the strains of powdery mildew fungus found in the Yakima Valley, Wash.: Treasure Valley, Id.; and Willamette Valley, Oreg. as of 2010, but since not all strains are present in the U.S. no future powdery mildew resistance can be assured. 'Delta' appears to be tolerant to strains of Verticillium wilt, and the virus diseases found in the USA growing areas. Susceptibility to hop downy mildew fungus is slight, even in the Willamette Valley, although preventative control measures are recommended in known downy mildew growing areas. Tolerance to the major soil borne pests and diseases that affect hops is not known at this time.

8. Regional adaptation: The 'Delta' variety is well adapted to the drier growing regions of Washington State and Idaho State specifically the Yakima Valley and the Treasure Valley. 'Delta' was tested in the Willamette Valley of Oregon from 2008-2010 and appears to be suitable to this area even with the higher humidity and the threat of downy mildew infections.

9. Ploidy: Hop variety 'Delta' is diploid. The mother is diploid and the father is diploid.

10. Life expectancy: Indefinite, similar to other hop varieties.

11. Use: Flavoring and conditioning of beverages and foods and use as a vegetable. Constituent of herbal remedies, nutraceuticals, pharmaceuticals, drugs, ointments, antiseptic washes, and cosmetics for humans and animals. Constituent of fodder, bedding, compost, agricultural treatments, phytoremediation treatments, water and soil treatments, conditioning of fermentation and other industrial processes. Used in breeding novel hop varieties.

12. Propagation status: 'Delta' rootstock and plant propagation material exists. Asexual plant propagation has been demonstrated.

13. Reproductive status: 'Delta' is fertile and produces seeds upon pollination with male hop plants.

DISTINGUISHING CHARACTERISTICS

This new hop variety 'Delta' can be distinguished from all other USA commercial aroma varieties known to the Inventor by its combination of powdery mildew resistance, good yield, excellent aroma, low CoH, 1:1 ratio of alpha-acids to beta-acids, good storage stability, high Linalool and low Farnesene.

We claim:

1. A new and distinct aroma hop plant, named 'Delta' as herein described and illustrated.

* * * * *